ly(e) United States Patent [19]
Wright et al.

[11] 4,095,023
[45] June 13, 1978

[54] 6-METHOXY-N-VANILLYLIDENE-4-CHROMANAMINE

[75] Inventors: George C. Wright; Marvin M. Goldenberg, both of Norwich, N.Y.

[73] Assignee: Morton-Norwich Products, Inc., Norwich, N.Y.

[21] Appl. No.: 812,105

[22] Filed: Jul. 1, 1977

[51] Int. Cl.² .................................. C07D 311/68
[52] U.S. Cl. .................................................. 542/422
[58] Field of Search ........................ 542/422, 423; 260/345.2

[56] References Cited
U.S. PATENT DOCUMENTS 3,004,969 10/1961 Paige ................................ 542/422
3,272,806 9/1966 Winterstein ..................... 542/422

Primary Examiner—Arthur P. Demers
Attorney, Agent, or Firm—Anthony J. Franze

[57] ABSTRACT

The compound 6-methoxy-N-vanillylidene-4-chromanamine is useful as an anti-inflammatory.

1 Claim, No Drawings

6-METHOXY-N-VANILLYLIDENE-4-CHROMANAMINE

This invention is concerned with the chemical compound 6-methoxy-N-vanillylidene-4-chromanamine. This compound possesses anti-inflammatory properties. For example, when administered p.o. to rats at a dose of about 300 mg/kg in a suspension of aqueous methyl cellulose, carageenin induced edema is suppressed. [Winter et al. P.S.E.B.M. 111:544 (1962)].

This compound can be readily compounded in the usual pharmaceutical dosage forms such as elixirs, tablets, capsules, suspensions and the like using commonly employed carriers and excipients of the pharmaceutical art with which there is no incompatibility.

In order that this invention may be readily available to and understood by those skilled in the art, the currently preferred method of making it is set forth:

A. 6-Methoxy-4-chromanone Oxime

A solution of 140 g (2102 mole) of hydroxylamine hydrochloride in 630 ml. of water, contained in a 3-l. Erlenmeyer flask, was treated with 560 ml. of ethanol, all with rapid stirring. The reaction mixture was heated to boiling over 15 min., and continued to boil for 5 min. The mixture was stirred rapidly at room temperature for 3 hrs., refrigerated overnight and filtered. A white crystalline solid was washed with 1 l. of water and air dried for three days. m.p. 120°–121°. Yield: 266 g. (99%).

B. 6-Methoxy-4-chromanamine Hydrochloride

A 123-g. (0.64 mole) portion of 6-methoxy-4-chromanone oxime and 540 ml. of ethanol were placed in a 1-l. pressure bottle, along with 32 g. (wet basis) of Raney nickel catalyst previously washed with ethanol to remove excess water. The mixture was subjected to hydrogenation at 49 psig. The hydrogen uptake was 90 lb. (theory 98 lb. at 27°) in 7 hrs. The reduction mixture was filtered, stripped under a water pump to one-third volume, treated with 113 ml. of isopropanol-HCl, pH 2, refrigerated overnight, and filtered. The resultant white crystalline solid was washed with 100 ml. of isopropanol, ether and dried. m.p. 223–224 decompn. Yield: 94 g. (68%).

The crude product was recrystallized from 1.2 l. of ethanol (Darco), washed with 120 ml. of ethanol, 240 ml. of ether, and dried; m.p. 220°–222° dec. Yield: 54 g. (39%).

Anal. Calcd. for $C_{10}H_{13}NO_2 \cdot HCl$: C, 55.68; H, 6.54; N, 6.50.

Found: C, 55.50; H, 6.52; N, 6.38.

C. 6-Methoxy-N-vanillylidene-4-chromanamine

A 70 g. (0.31 mole) portion of B., and 390 ml. of ethanol were placed in a 2 l., 3-necked flask, equipped with a stirrer and reflux condenser with a drying tube. The slurry was treated with 53 g. (0.35 mole) of vanillin, refluxed for 5 hrs., and filtered hot. The filtrate was refrigerated overnight, and filtered. The cream solid was washed with 100 ml. of ethanol, ether and dried; m.p. 136°–139°. Yield: 98 g. (100%).

The product was recrystallized from 700 ml. of isopropanol, washed with 100 ml. of isopropanol-ether and dried; m.p. 136°–138°. Yield: 91 g. (93%).

Anal. Calcd. for $C_{18}H_{19}NO_4$ : C, 68.99; H, 6.11; N, 4.47.

Found: C, 68.76; H, 6.18; N, 4.28.

What is claimed is:

1. The compound 6-methoxy-N-vanillylidene-4-chromanamine.